United States Patent
Streeter et al.

(10) Patent No.: US 10,625,031 B2
(45) Date of Patent: *Apr. 21, 2020

(54) ORIENTATION INDEPENDENT TOPICAL APPLICATOR

(71) Applicant: L'OREAL, Paris (FR)

(72) Inventors: John Streeter, Redmond, WA (US); Zane Bowman Allen Miller, Seattle, WA (US); Vincenzo Casasanta, III, Woodinville, WA (US)

(73) Assignee: L'OREAL, Paris (FR)

( * ) Notice: Subject to any disclaimer, the term of this patent is extended or adjusted under 35 U.S.C. 154(b) by 465 days.

This patent is subject to a terminal disclaimer.

(21) Appl. No.: 15/391,323

(22) Filed: Dec. 27, 2016

(65) Prior Publication Data

US 2018/0177957 A1    Jun. 28, 2018

(51) Int. Cl.
*A61M 11/00* (2006.01)
*A61M 35/00* (2006.01)
*A61M 37/00* (2006.01)

(52) U.S. Cl.
CPC ........ *A61M 11/005* (2013.01); *A61M 35/003* (2013.01); *A61M 37/0092* (2013.01); *A61M 2205/13* (2013.01); *A61M 2205/21* (2013.01); *A61M 2205/3389* (2013.01); *A61M 2205/502* (2013.01); *A61M 2205/6018* (2013.01); *A61M 2205/6063* (2013.01); *A61M 2205/82* (2013.01)

(58) Field of Classification Search
CPC ............ A61M 11/005; A61M 37/0092; A61M 35/003; A61M 2205/6063; A61M 2205/21; A61M 2205/33; A61M 2205/82; A61M 2205/502; A61M 2205/6018
See application file for complete search history.

(56) References Cited

U.S. PATENT DOCUMENTS

| 4,319,716 A | 3/1982 | Lauer | |
| 9,357,961 B2* | 6/2016 | Arefieg | A61B 5/157 |
| 2003/0146300 A1* | 8/2003 | Denyer | A61M 11/00 239/338 |
| 2006/0201501 A1* | 9/2006 | Morrison | A61M 15/0085 128/203.27 |

(Continued)

FOREIGN PATENT DOCUMENTS

| EP | 1 935 280 A1 | 6/2008 |
| EP | 2 140 943 A1 | 1/2010 |

(Continued)

*Primary Examiner* — Amber R Stiles
(74) *Attorney, Agent, or Firm* — Oblon, McClelland, Maier & Neustadt, L.L.P.

(57) ABSTRACT

An ultrasonic topical applicator and method is provided for dispensing a topical including an adjustable head including a mesh nebulizer having a perforated plate with a plurality of pores and a vibrating actuator, a cartridge having a reservoir for holding a topical and a port configured to secure the reservoir to the mesh nebulizer, and a handle including a power source and a controller configured to control energy from the power source to the mesh nebulizer based on an energy profile, where the vibrating actuator is configured to produce ultrasonic vibration based on the energy profile, and where the adjustable head is configured to lock into within the handle and to allow the adjustable head to rotate.

11 Claims, 8 Drawing Sheets

(56) References Cited

U.S. PATENT DOCUMENTS

| | | | |
|---|---|---|---|
| 2010/0222752 A1* | 9/2010 | Collins, Jr. | A61M 11/005 |
| | | | 604/296 |
| 2011/0262208 A1 | 10/2011 | Edmondson et al. | |
| 2014/0352689 A1* | 12/2014 | Seshadri | A61M 15/0085 |
| | | | 128/200.16 |
| 2016/0331106 A1* | 11/2016 | Khormaei | A46B 7/08 |
| 2018/0280633 A1* | 10/2018 | Miller | B05B 12/10 |

FOREIGN PATENT DOCUMENTS

| | | |
|---|---|---|
| EP | 2 380 456 A1 | 10/2011 |
| WO | WO 99/38621 A1 | 8/1999 |

\* cited by examiner

FIG. 5A
500a

```
       Start
         ↓
┌─────────────────────────────────────┐  ─ 502
│ Control delivery of energy from      │
│ power source to mesh nebulizer       │
└─────────────────────────────────────┘
         ↓
        End
```

FIG. 5B
500b

```
            Start
              ↓
┌─────────────────────────────────┐ ─ 510
│      Detect proximity distance   │
└─────────────────────────────────┘
              ↓
┌─────────────────────────────────┐ ─ 512
│ Compare proximity distance to    │
│        proximity threshold       │
└─────────────────────────────────┘
              ↓
┌─────────────────────────────────┐ ─ 514
│ Determine energy profile based   │
│      on the proximity distance   │
└─────────────────────────────────┘
              ↓
┌─────────────────────────────────┐ ─ 516
│ Control delivery of energy from  │
│ power source to mesh nebulizer   │
│ based on at least one of the     │
│ comparison and the determination │
└─────────────────────────────────┘
              ↓
             End
```

Start → 520 Detect cartridge type → 522 Determine energy profile based on cartridge type → 524 Control delivery of energy from power source to mesh nebulizer based on the energy profile → End

Start → 530 Detect cartridge status → 532 Determine energy profile based on cartridge status → 534 Control delivery of energy from power source to mesh nebulizer based on the energy profile → 536 Control indicator based on the determination → End

*538*: feedback loop from 534 back to 530

Start
↓
540 Detect orientation
↓
542 Determine energy profile based on the orientation
↓
544 Control delivery of energy from power source to mesh nebulizer based on the energy profile
↓
546 Control indicator based on the determination
↓
End

*548* (feedback loop from 544 back to 540)

Start
↓
550 Detect orientation and cartridge status
↓
552 Determine device status based on orientation and cartridge status
↓
554 Control indicator based on the determination
↓
End

ORIENTATION INDEPENDENT TOPICAL APPLICATOR

BACKGROUND

The present disclosure describes a personal care appliance for use in skincare including an orientation-independent topical applicator.

SUMMARY

An ultrasonic topical applicator and method is provided for dispensing a topical including an adjustable head including a mesh nebulizer having a perforated plate with a plurality of pores and a vibrating actuator, a cartridge having a reservoir for holding a topical and a port configured to secure the reservoir to the mesh nebulizer, and a handle including a power source and a controller configured to control energy from the power source to the mesh nebulizer based on an energy profile, where the vibrating actuator is configured to produce ultrasonic vibration based on the energy profile, and where the adjustable head is configured to lock into within the handle and to allow the adjustable head to rotate.

BRIEF DESCRIPTION OF THE DRAWINGS

A more complete appreciation of the disclosed embodiments and many of the attendant advantages thereof will be readily obtained as the same becomes better understood by reference to the following detailed description when considered in connection with the accompanying drawings, wherein:

FIG. 5A is a flow diagram describing a method for dispensing a topical according to an example;

FIG. 5B is a flow diagram describing a method for dispensing a topical based on a proximity distance according to an example;

FIG. 5C is a flow diagram describing a method for dispensing a topical based on a cartridge type according to an example;

FIG. 5D is a flow diagram describing a method for dispensing a topical based on a cartridge status according to an example;

FIG. 5E is a flow diagram describing a method for dispensing a topical based on an orientation according to an example; and FIG. 5F is a flow diagram describing a method for dispensing a topical based on the orientation and the cartridge status according to an example.

DETAILED DESCRIPTION

Figure 1A:
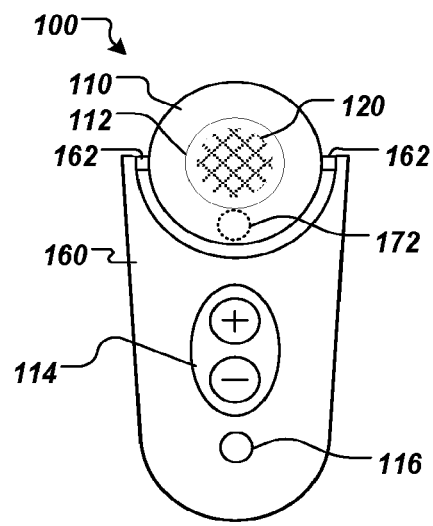
FIG. 1A is drawing of front view of an ultrasonic topical applicator including a housing having an aperture, a mesh nebulizer, and a user control interface according to an example.

Referring now to the drawings, wherein like reference numerals designate identical or corresponding parts throughout the several views.

Ultrasonic mesh nebulizer technology is utilized in applicators, pulmonary inhalers, home misting and other devices intended to provide a fine spray for small particle size, greater distribution or surface coverage. An ultrasonic topical applicator (UTA) device 100 is provided for dispensing of a topical in a spray regardless of orientation when held. In some implementations, components of the UTA device can be divided into an adjustable housing and a handle, where the adjustable housing can be oriented independently of the handle such that the topical can consistently be in contact with the mesh nebulizer regardless of orientation. Examples of topicals include fluids, cosmetics, sunscreen, perfumes, repellants, etc. In an example, the topical can have a known viscosity or topical viscosity.

FIG. 1A is drawing of a front view of a UTA device 100 including an adjustable head 110 configured to lock into a slot or full socket 162 within a handle 160, allowing the adjustable head 110 to rotate in a single axis or multiple axes. In an example, the adjustable head 110 can have an aperture 112, a mesh nebulizer 120 having a plurality of pores, a cartridge 130 having a reservoir for holding a topical. In an example, the aperture 112 can act as a nozzle that can direct the spray in one direction or another (not shown). In an example, the handle 160 can have a user control interface 114 configured to receive a user input, an indicator 116 configured to indicate a notice to the user, a controller 140 in communication with a power source 150, and circuitry 142, 144 configured to connect electrical components within the handle 160 as well as between the adjustable head 110 and the handle 160 (See FIG. 1B).

In an example, the adjustable head 110 can include one or more of an actuator, a valve, a controllable aperture, an electromechanical orifice, an aperture diaphragm, an electromechanical port, and the like. In an example, the adjustable head 110 can include one or more electronic oscillators for controlling a nebulizer, an ultrasonic vibrating mesh, an electromechanical spray valve, and the like.

In an example, the mesh nebulizer 120 includes a thin metal mesh that is connected to a vibrating actuator 220 configured to produce ultrasonic vibration when energized at a particular energy profile 180 including a frequency and power. A representative energy profile 180 can include a frequency of 120 KHz and power of 5 W. When a surface of the mesh nebulizer 120 is placed in contact with the topical, vibration of the mesh nebulizer 120 is configured to eject droplets of the topical from the plurality of pores, forming a spray 440 (See FIGS. 4B-4C). In an example, the UTA device 100 is configured to eject the spray 440 using the controller 140 to control the energy profile 180 delivered from the power source 150 to the mesh nebulizer 120. In an example, the energy profile 180 can vary an intensity of the spray 440. In an example, the energy profile 180 can be based on a type of topical or the topical viscosity. In an example, the energy profile 180 can be determined by sensing an identifier 324 or a cartridge sensor 342-346 as described below. In an example, the energy profile 180 can be determined by receiving an input from the user control interface 114.

Mesh Nebulizer

In some implementations, the mesh nebulizer 120 can be made from a perforated plate 210 having a mesh portion 212 and a vibrating actuator 220. In an example, the mesh 212 of the perforated plate 210 can be made from a plurality of pores through the perforated plate 210. In an example, the perforated plate 210 can be made from a thin metal or a ceramic configured to vibrate at ultrasonic frequencies. In an example, the mesh nebulizer 120 can be a microporous atomizer high output mesh from Steiner & Martins, INC. (Doral, Fla.)

In an aspect, each pore can be configured to prevent leaking of the topical. In an example, each pore can be configured to eject the topical based on the topical viscosity. In an example, each pore can have a circular shape with a diameter of 5μ to 20μ. In an example, the plurality of pores can be laser drilled through the perforated plate 210. In another example, the perforated plate 210 can be manufactured with the plurality of pores using Microelectromechanical systems (MEMS) processing technology.

FIGS. 2A-2B each show a drawing of a top and side view respectively of a mesh nebulizer 120*a* having a disk shape according to an example. In an example, the vibrating actuator 220 is made of a piezoelectric material bonded to at least one side of the perforated plate 210. As best shown is FIG. 2B, the vibrating actuator 220 can be made from a top piezoelectric material 220*a* and a bottom piezoelectric material 220*b* that sandwich the perforated plate 210.

FIGS. 2C-2D each show a drawing of a top and side view respectively of a mesh nebulizer 120*b*' having a rectangular shape according to an example. As best shown is FIG. 2C, the vibrating actuator 220 can be made from a top piezoelectric material 220*a* and a bottom piezoelectric material 220*b* that sandwich the perforated plate 210.

FIG. 2E shows a drawing of a side view respectively of a mesh nebulizer 120*b*" having a rectangular shape according to another example. The mesh nebulizer 120" includes a vibrating actuator 220 bonded to only one side of the perforated plate 210.

Cartridge

The UTA device 100 can be configured to maintain the topical at the mesh 212, independent of orientation, in several ways. In some implementations, the cartridge 130 can include a reservoir 310*a-c* configured to hold the topical with a positive pressure. In some implementations, the cartridge 130 can include a coupling port 320 configured to hold at least a portion of the topical at the mesh 212.

The cartridge 130 can have a coupling port 320 configured to mate or secure the cartridge 130 with the adjustable head 110. In an example, the coupling port 320 can include a gasket 322 for enhancing a connection to the mesh nebulizer 120. In an example, the coupling port 320 can include an identifier 324 configured to identify at least one of a cartridge type and a cartridge status. In an example, the cartridge type can indicate a type of topical in the reservoir 310*a-c*. Examples of the cartridge status can include an indication of an amount of topical in the reservoir 310*a-c*, an expiration date of the topical, and a sensor reading from a cartridge sensor 342-346 as described below.

In an example, each cartridge 130*a-c* can have a reservoir 310*a-c* with a predetermined topical and the identifier 324 can be configured to encode or indicate the predetermined topical. In an example, the identifier 324 can be a label or printing on the cartridge 130. In another example, the identifier 324 can be a form of programmable memory. In an aspect, the identifier 324 can be configured to connect the cartridge sensor 342-346 to the circuitry 142, 144 and the controller 140.

In an example, the cartridge 130*a-c* can have a mesh interface 312 configured to maintain freshness of the topical. In an example, the mesh interface 312 can be removable prior to assembly of the cartridge 130*a-c* to the adjustable head 110.

Capillary Action Tray

As shown in FIG. 3A, in an example, a cartridge 130*a* can include the mesh interface 312, a gasket 322, and a reservoir 310*a* having a chamber volume for storing the topical, and a capillary action tray 330 configured to hold at least a portion of the topical at the mesh 212 and/or mesh interface 312 using capillary action. In an example, the capillary action tray 330 can include an inner reservoir 332 configured to have an area similar to the mesh 212 and a tray depth 334 configured to facilitate capillary action with the mesh 212 and/or mesh interface 312. In an example, the capillary action tray 330 can optionally include one or more tubes 336 configured to replenish the inner reservoir 332. Each tube 336 can be sized to facilitate capillary motion and can be generally perpendicular to the mesh face. In an example, the cartridge 130*a* can optionally further include the identifier 324 and a cartridge sensor 342 configured to detect an amount of topical within the capillary action tray 330 and/or the reservoir 310*a*. In an example, the capillary action tray 330 can be considered as part of the coupling port 320.

Wick/Wadding

As shown in FIG. 3B, in an example, a cartridge 130*b* can include a mesh interface 312, and a reservoir 310*b* having a wick or wadding 350 configured to hold at least a portion of the topical at the mesh 212 and/or mesh interface 312. In an example, the wick or wadding 350 can be made from cotton or textile configured to be saturated with the topical. In an example, the wick 350 can be configured to take advantage of capillary action to maintain topical at the mesh 212 and/or mesh interface 312.

In an example, the cartridge 130*b* can optionally further include the identifier 324 and a cartridge sensor 344 configured to detect an amount of topical within the wick or wadding 350 and/or the reservoir 310*b*. In an example, the cartridge sensor 344 can have at least two conductive wires or contacts that can be shorted when the topical is sufficiently within the wick or wadding 350. In an example, the cartridge sensor 344 can have at least two conductive contacts or plates across the wick or wadding 350, configured to have a varying capacitance based on an amount of topical within the wick or wadding 350. In an example, the wick or wadding 350 can be considered as part of the coupling port 320.

Diaphragm

Figure 3A:
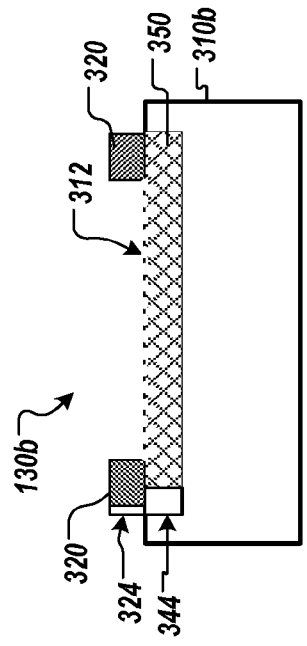
FIG. 3A shows a cross-section drawing of a cartridge having a reservoir including a capillary action tray configured to hold at least a portion of the topical at the mesh nebulizer according to an example.
Figure 3B:
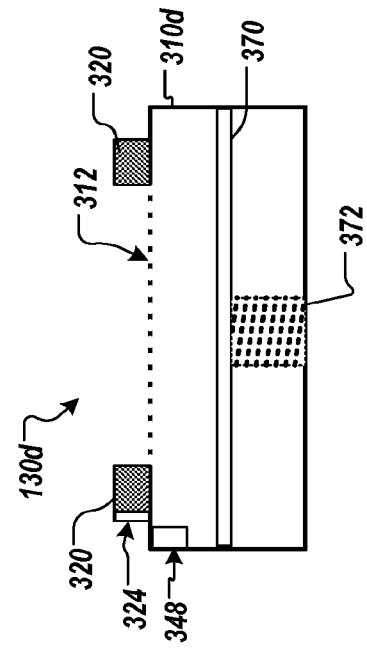
FIG. 3B shows a cross-section drawing of a cartridge having a reservoir including a wick or wadding configured to hold at least a portion of the topical at the mesh nebulizer according to an example.
Figure 3C:
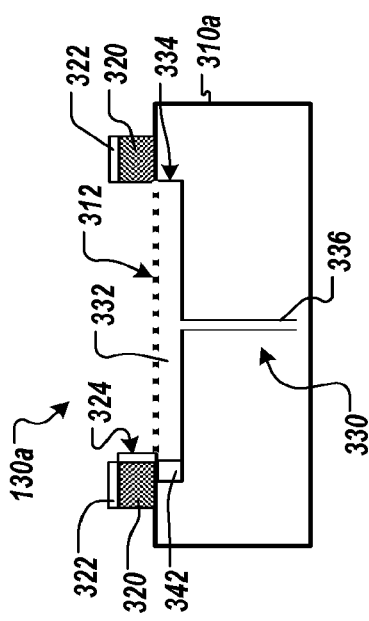
FIG. 3C shows a cross-section drawing of a cartridge having a reservoir including a diaphragm configured to hold at least a portion of the topical at the mesh nebulizer according to an example.

As shown in FIG. 3C, in an example, a cartridge 130c can include a mesh interface 312 and a reservoir 310c having a diaphragm 360 configured to hold at least a portion of the topical at the mesh 212 and/or mesh interface 312. In an example, the diaphragm 360 can hold at least a portion of the topical at the mesh 212 and/or mesh interface 312 by decreasing a reservoir volume 362. In an example, by inflating a bladder (not shown), the diaphragm 360 can be moved from a first diaphragm position 360' to a second diaphragm position 360", where the reservoir volume 362 is decreased. In an example, the cartridge 130c can optionally further include the identifier 324 and a cartridge sensor 346 configured to detect an amount of topical within the wick or wadding 350 and/or the reservoir 310b.

Plunger

Figure 3D:
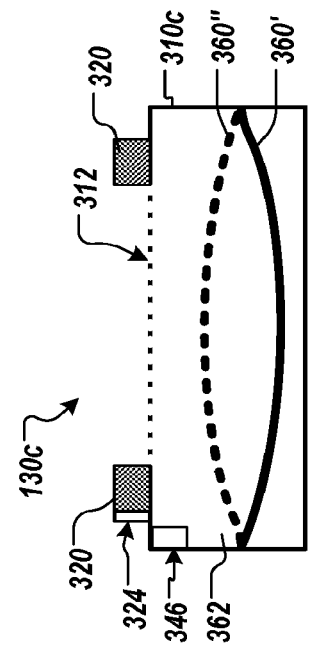
FIG. 3D shows a cross-section drawing of a cartridge having a reservoir including a plunger configured to deliver the topical at the mesh nebulizer according to an example.

As shown in FIG. 3D, in an example, a cartridge 130d can include a reservoir 310d having a plunger 370 configured to modify the reservoir volume and deliver the topical at the mesh nebulizer 120. In an example, the plunger 370 can store the topical at a negative pressure such that the plunger 370 is configured to automatically reduce the reservoir volume during ejection of the topical. In another embodiment, the adjustable head 110 can have an actuator 372 configured to move the plunger 370 based on the controller 140. Examples of the actuator 372 can include a linear actuator, a pneumatic actuator, and a syringe pump.

Positioning Sensor

In some implementations, the UTA device 100 can include one or more positioning sensors configured to sense at least one of an orientation of the UTA device 100 relative to gravity and a proximity of the UTA device 100 and the adjustable head 110 relative to the skin of the user.

Orientation Sensor

Figure 1B:
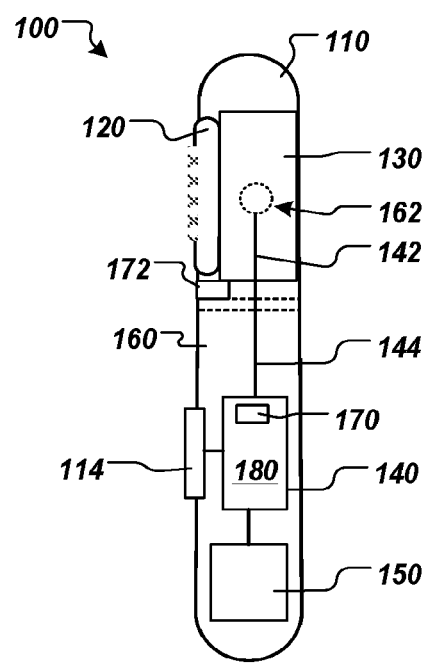
FIG. 1B is drawing of side view of the ultrasonic topical applicator showing internal components including a cartridge having a reservoir for holding a topical, a controller, a power source, and circuitry according to an example.
Figure 2A:
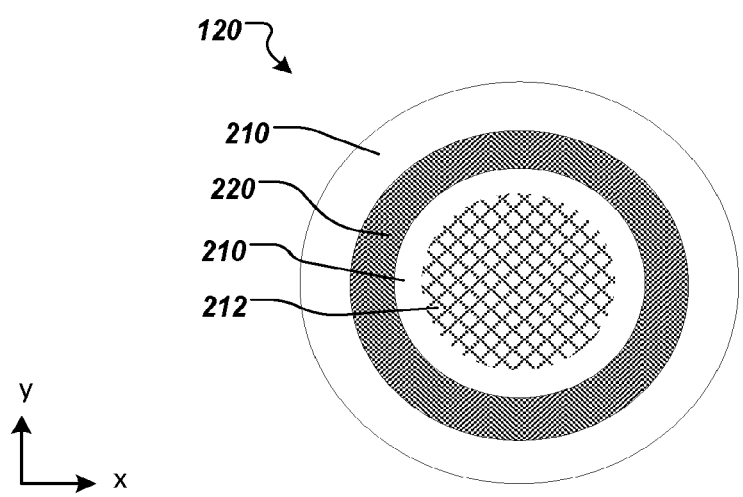
FIG. 2A is a drawing of a top view of a mesh nebulizer having a disk shape according to an example.
Figure 2B:
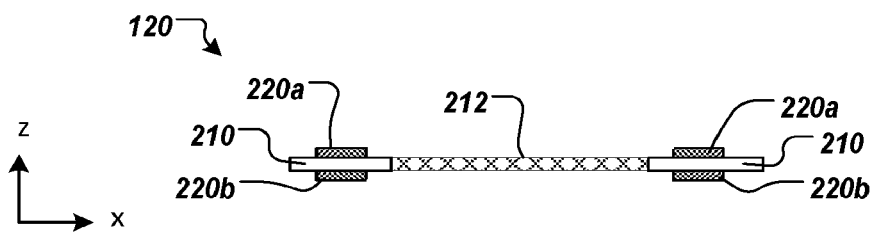
FIG. 2B is a drawing of a side view of the mesh nebulizer having a disk shape according to an example.
Figure 2C:
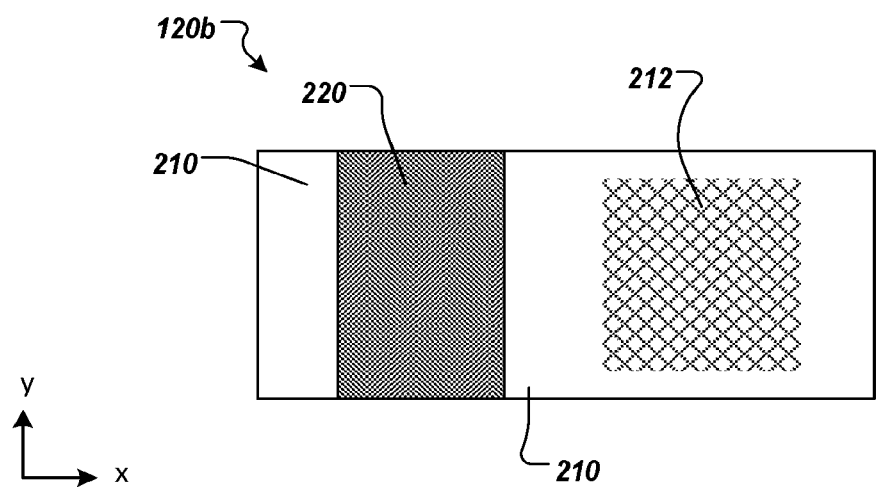
FIG. 2C is a drawing of a top view of a mesh nebulizer having a rectangular shape according to an example.
Figure 2D:
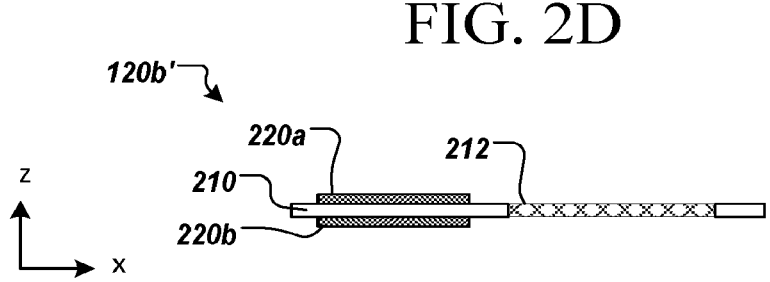
FIG. 2D is a drawing of a side view of a mesh nebulizer having a rectangular shape according to an example.
Figure 2E:
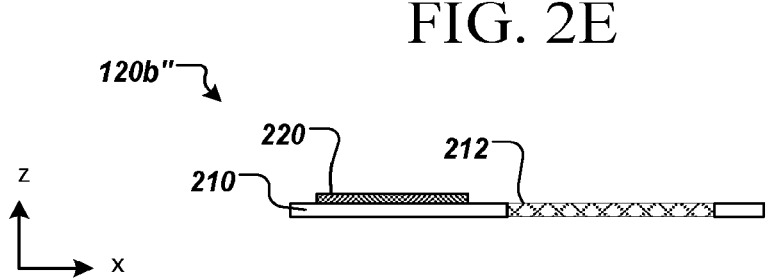
FIG. 2E is a drawing of a side view of a mesh nebulizer having a rectangular shape according to another example.

As shown in FIG. 1B, in an example, the handle 160 can include an orientation sensor 170 configured to sense an orientation of the UTA device 100 relative to gravity. In an example, the adjustable head 110 can include an orientation sensor 170 configured to sense an orientation of the adjustable head 110 relative to gravity or the handle 160. Examples of orientation sensors can include a gyroscope, a magnetometer, as well as a fluidic detector configured to electrically short a pair of electrical contacts or vary a capacitance, etc.

Proximity Sensor

As shown in FIGS. 1A-1B, 4A-4B, the adjustable head 110 can include a proximity sensor 172 configured to sense a proximity distance 430a-b of the adjustable head 110 to the skin 420 of the user according to an example. Examples of proximity sensors can include ultraviolet and infrared detector/emitters, sonic detector/emitters, optical sensors, etc.

Figure 4A:
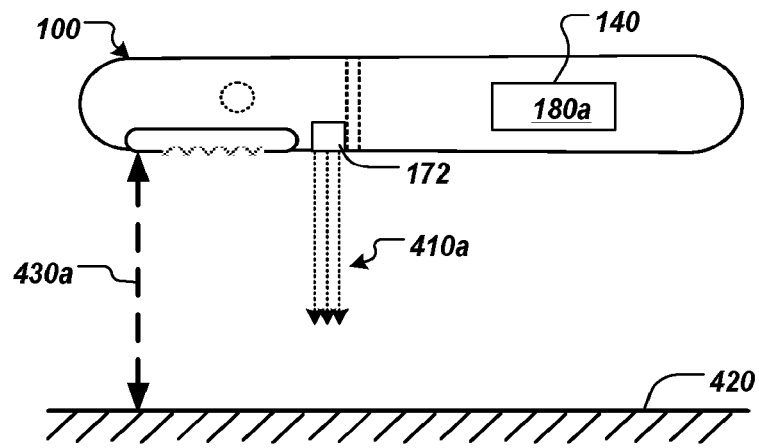
FIGS. 4A-4B each show a drawing of the ultrasonic topical applicator including a proximity sensor configured to sense a proximity distance to the skin of the user and to control energy delivered from the power source to the mesh nebulizer based on the proximity distance according to an example.
Figure 4B:
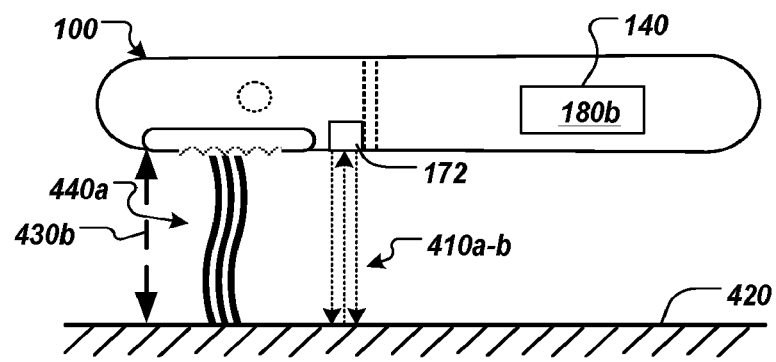

As illustrated in FIGS. 4A-4B, the proximity sensor 172 can be configured to detect the proximity distance 430a-b using an emitted wave 410a and a reflected wave 410b. In an example, the controller 140 can be configured to compare the proximity distance 430 to a proximity threshold. In an example, the proximity threshold can be set using the user control interface 114. In an example, the proximity sensor 172 can be configured to be connected in-line between the controller 140 and the mesh nebulizer 120 such that the proximity sensor 172 cuts power when the proximity threshold is not met. In an example, the proximity threshold for a gentle refreshing water mist application can be around 1"-2" inches from the skin surface whereas, the proximity threshold for a higher flow or a coverage'spray such as for sunscreen application can be around 6"-10" inches from the skin surface.

FIG. 4A shows the UTA device 100 detecting a proximity distance 430 greater than the proximity threshold. Subsequently, the controller 140 is configured to control the energy delivered from the power source 150 to the mesh nebulizer 120 based on an energy profile 180a. In an example, the energy profile 180a can be configured to deliver no energy.

FIG. 4B shows the UTA device 100 detecting a proximity distance 430 within the proximity threshold. Subsequently, the controller 140 is configured to control the energy delivered from the power source 150 to the mesh nebulizer 120 based on an energy profile 180b. In an example, the energy profile 180b can be configured to deliver energy configured to eject the topical towards the skin 420 in a spray 440a.

Figure 4C:
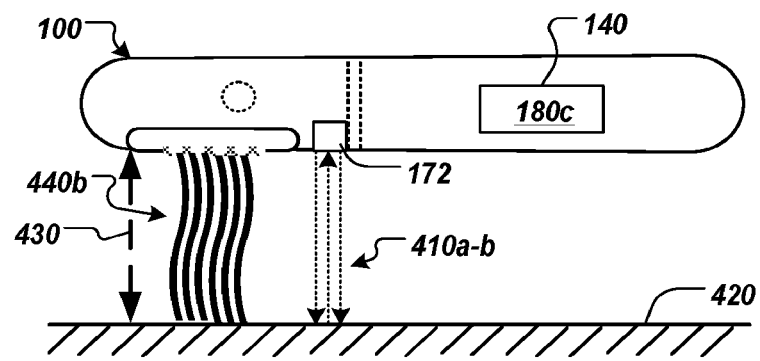
FIG. 4C shows a drawing of the ultrasonic topical applicator of FIGS. 4A-4B configured to control energy delivered from the power source to the mesh nebulizer based on the energy profile according to an example.

FIG. 4C shows a drawing of the UTA device 100 shown in of FIGS. 4A-4B configured to control the energy delivered from the power source 150 to the mesh nebulizer 120 based on a modified energy profile 180c. In an example, the modified energy profile 180c can be configured to deliver energy configured to eject the topical towards the skin 420 in a spray 440b. In an example, the spray can vary in intensity as required by the topical and application.

Controller

In an example, the UTA device 100 is configured to dispense or eject a topical spray 440 by using the controller 140 to control the energy delivered from the power source 150 to the mesh nebulizer 120. In some implementations, the controller 140 is configured to control the energy profile 180 for delivering energy from the power source 150 to the mesh nebulizer 120 based on the one or more positioning sensors and the cartridge sensors 342-346. In some embodiments, the controller 140 incudes a programmable microcontroller or processor (not shown), which is configured to control the energy delivered from the power source 150 to the mesh nebulizer 120.

FIG. 5A is a flow diagram describing a method 500a for dispensing a topical according to an example. The method 500a includes a step of controlling delivery of energy from the power source 150 to the mesh nebulizer 120 (502). An example of step 502, controlling delivery of energy from the power source 150 to the mesh nebulizer 120, can be using a default energy profile 180. In an example, the default energy profile 180 can be set using the user control interface 114.

An example of step 502, can be controlling, using a controller 140, delivery of energy based on an energy profile 180 from a power source 150 to a mesh nebulizer 120 having a perforated plate with a plurality of pores and a vibrating actuator, where the vibrating actuator is configured to produce an ultrasonic vibration based on the energy profile, where the topical is nebulized when in contact with the perforated plate vibrating with the ultrasonic vibration, and where the nebulized topical forms a spray dispensing the topical.

Dispensing a Topical Based on a Proximity Distance

FIG. 5B is a flow diagram describing a method 500*b* for dispensing a topical based on a proximity distance according to an example. The method 500*b* includes steps of detecting a proximity distance (510), comparing the proximity distance to a proximity threshold determining an energy profile 180 based on the proximity distance (512), optionally determining an energy profile 180 based on the proximity distance (514), and controlling delivery of energy from the power source 150 to the mesh nebulizer 120 based on at least one of the comparison 512 and the determination 514 or the energy profile 180 (516). Optionally, the method 500*b* can further include a step of returning to step 510 (518).

An example of step 514, determining an energy profile 180 based on the proximity distance, can be modifying a frequency and/or power of the energy profile 180 based on the proximity distance 430 detected by the proximity sensor 172.

Dispensing a Topical Based on a Cartridge Type

FIG. 5C is a flow diagram describing a method 500*c* for dispensing a topical based on a cartridge type according to an example. The method 500*c* includes steps of detecting a cartridge type (520), determining an energy profile 180 based on the cartridge type (522), and controlling delivery of energy from the power source 150 to the mesh nebulizer 120 based on the energy profile 180 (524).

An example of step 522, determining an energy profile 180 based on the cartridge type, can be modifying a frequency and/or power of the energy profile 180 based on the topical type identified by the identifier 324.

Dispensing a Topical Based on a Cartridge Status

FIG. 5D is a flow diagram describing a method 500*d* for dispensing a topical based on a cartridge status according to an example. The method 500*d* includes steps of detecting a cartridge status (530), determining an energy profile 180 based on the cartridge status (532), and controlling delivery of energy from the power source 150 to the mesh nebulizer 120 based on the determination 532 or the energy profile 180 (534). Optionally, the method 500*d* can further include a step of controlling an indicator 116 based on the determination 532 (536). Optionally, the method 500*d* can further include a step of returning to step 530 (538).

An example of step 532, determining an energy profile 180 based on the cartridge status, can be modifying a frequency and/or power of the energy profile 180 based on the amount of topical in the reservoir 130 sensed by the cartridge sensor 342-346.

Dispensing a Topical Based on an Orientation

FIG. SE is a flow diagram describing a method 500*e* for dispensing a topical based on an orientation according to an example. The method 500*e* includes steps of detecting an orientation (540), determining an energy profile 180 based on the detected orientation (542), and controlling delivery of energy from the power source 150 to the mesh nebulizer 120 based on the determination 542 or the energy profile 180 (544). Optionally, the method 500*e* can further include a step of controlling an indicator 116 based on the determination 542 (546). Optionally, the method 500*e* can further include a step of returning to step 540 (548).

An example of step 540, detecting an orientation, can include inferring an orientation of the mesh nebulizer 120 by sensing the orientation sensor 170 on the adjustable head 110.

An example of step 542, determining an energy profile 180 based on the detected orientation, can be modifying a frequency and/or power of the energy profile 180 based on the amount of topical in the reservoir 130 sensed by the cartridge sensor 342-346.

An example of step 544, controlling an indicator 116 based on the determination 542, can be configuring the indicator 116 to indicate that the amount of topical in the reservoir 130 sensed by the cartridge sensor 342-346 is below a particular amount for the detected orientation.

Dispensing a Topical Based on an Orientation and a Cartridge Status

FIG. 5F is a flow diagram describing a method 500*f* for dispensing a topical based on an orientation and a cartridge status according to an example. The method 500*f* includes steps of detecting an orientation and a cartridge status (550), determining a device status based on the orientation and the cartridge status (552), and controlling an indicator 116 based on the determination 552 (554).

An example of step 554, controlling an indicator 116 based on the determination 552, can be configuring the indicator 116 to indicate that the amount of topical in the reservoir 130 sensed by the cartridge sensor 342-346 is below a particular amount.

Obviously, numerous modifications and variations of the present disclosure are possible in light of the above teachings. It is therefore to be understood that within the scope of the appended claims, the invention may be practiced otherwise than as specifically described herein.

The invention claimed is:

1. An ultrasonic topical applicator for dispensing a topical, the applicator comprising:
    an adjustable head including a mesh nebulizer having a perforated plate with a plurality of pores and a vibrating actuator;
    a cartridge having a reservoir for holding a topical formulation and a port configured to secure the reservoir to the mesh nebulizer; and
    a handle including a power source and a controller configured to control energy from the power source to the mesh nebulizer based on an energy profile, wherein the energy profile determines a drive frequency and power of the vibrating actuator that is correlated to a property of the topical formulation,
    wherein the vibrating actuator is configured to produce ultrasonic vibration based on the energy profile,
    wherein the adjustable head is configured to lock into within the handle and to allow the adjustable head to rotate.

2. The ultrasonic topical applicator of claim 1, wherein the handle further includes a user control interface configured to set the energy profile.

3. The ultrasonic topical applicator of claim 1, further comprising an indicator configured to indicate a cartridge status.

4. The ultrasonic topical applicator of claim 1, wherein the cartridge includes a capillary action tray configured to hold at least a portion of the topical formulation at the mesh nebulizer.

5. The ultrasonic topical applicator of claim 1, wherein the cartridge includes a wick configured to hold at least a portion of the topical formulation at the mesh nebulizer.

6. The ultrasonic topical applicator of claim 1, wherein the cartridge includes a diaphragm configured to hold at least a portion of the topical formulation at the mesh nebulizer.

7. The ultrasonic topical applicator of claim 1, wherein the reservoir is configured to hold the topical with a positive pressure.

8. The ultrasonic topical applicator of claim 1, wherein the cartridge includes an identifier configured to identify at least one of a cartridge type and a cartridge status.

9. The ultrasonic topical applicator of claim 1, wherein the cartridge includes a cartridge sensor, and wherein the controller is configured to set the energy profile based on the cartridge sensor.

10. The ultrasonic topical applicator of claim 1, further comprising a proximity sensor configured to detect a proximity distance to a skin of the user,
wherein the controller is configured to set the energy profile based on the proximity distance.

11. The ultrasonic topical applicator of claim 1, further comprising an orientation sensor configured to detect an orientation of the adjustable head,
wherein the controller is configured to set the energy profile based on the orientation.

* * * * *